United States Patent [19]
Gildenberg

[11] Patent Number: 5,855,582
[45] Date of Patent: Jan. 5, 1999

[54] NONINVASIVE STEREOTACTIC APPARATUS AND METHOD FOR RELATING DATA BETWEEN MEDICAL DEVICES

[76] Inventor: Philip L. Gildenberg, 3776 Darcus, Houston, Tex. 77005

[21] Appl. No.: 574,945

[22] Filed: Dec. 19, 1995

[51] Int. Cl.[6] .................................................. A61B 19/00
[52] U.S. Cl. ........................... 606/130; 600/417; 600/429
[58] Field of Search ........................... 606/1, 30; 600/407, 600/410, 414, 415, 417, 425, 426, 429

[56] References Cited

U.S. PATENT DOCUMENTS

| | | |
|---|---|---|
| 1,398,842 | 11/1921 | Cruse ....................................... 606/130 |
| 3,508,552 | 4/1970 | Hainault . |
| 3,841,148 | 10/1974 | Becker . |
| 4,228,799 | 10/1980 | Anichkov et al. . |
| 4,465,069 | 8/1984 | Barbier et al. .......................... 606/130 |
| 4,884,566 | 12/1989 | Mountz et al. . |
| 5,095,919 | 3/1992 | Monticelli et al. ....................... 606/56 |
| 5,171,296 | 12/1992 | Herman . |
| 5,423,832 | 6/1995 | Gildenberg . |

*Primary Examiner*—Glenn K. Dawson
*Attorney, Agent, or Firm*—Wood, Herron & Evans, L.L.P.

[57] ABSTRACT

A noninvasive alignment apparatus for providing a stereotactic interface between a noninvasive stereotactic adapter mounted on a patient's head and a medical device, such as, an imaging device or a radiotherapy machine. The apparatus permits a method of noninvasive fractionated radiotherapy to be practiced. The alignment apparatus is constructed of separable arcuate segments to facilitate the insertion of the patient's head and stereotactic adapter within the apparatus. The alignment apparatus further has various calibrated shafts for each of its movable elements, so that, after the alignment apparatus is initially positioned and adjusted on an imaging machine, its position with respect to the stereotactic adapter may be replicated later on a radiotherapy machine.

25 Claims, 6 Drawing Sheets

NONINVASIVE STEREOTACTIC APPARATUS AND METHOD FOR RELATING DATA BETWEEN MEDICAL DEVICES

FIELD OF THE INVENTION

This invention relates generally to the field of stereotactic procedures and devices and, more particularly, to a noninvasive alignment device and method for providing a stereotactic interface relating data established during preoperative diagnostic imaging procedures to a treatment device.

BACKGROUND OF THE INVENTION

Procedures which involve invasive surgery, radiation therapy or other procedures preformed on the brain or other intracranial structures are especially difficult for the patient. While significant advances have been made in stereotactic equipment and procedures to reduce the discomfort and stress suffered by a patient, most procedures still require the use of invasive stereotactic appliances both in the diagnostic and in the surgical or treatment procedures. For example, referring to FIG. 1, there is shown a "BRW"/"CRW"-type stereotactic head ring 10 disposed around the outside of a patient's head 11. The head ring 10 comprises an annular base 12 formed of metal. Four vertical brackets 13 extend upward from the inside diameter of the base 12. Four adjustable skull pins 14 are threadedly engaged with the upper portions of the brackets 13. The skull pins 14, when rotated relative to the brackets 13, extend inwardly to engage the patient's skull, or retract outwardly to disengage from the patient's skull. The skull pins 14 have pointed tips or ends 15 which, when the skull pins are extended inwardly, penetrate the outer tissue of the patient's head 11 and engage the bone of the skull so as to rigidly and invasively affix the head ring 10 to the patient's head.

The head ring 10 includes recessed ball sockets 16 into which the ball type connectors of compatible stereotactic devices may be received. For example, the head ring 10 is illustrated as supporting a localizing device, that is, a fiducial localizer, 17 used for establishing a coordinate system and measurement reference for diagnostic procedures. The localizing device 17 includes six vertical bars 18 and three inclined bars 19. When diagnostic scanning procedures such as magnetic resonance imaging ("MRI") or computerized axial tomography ("CAT scan") or the like are performed on a patient's head with the localizing device 17 in place, the vertical and inclined bars 18, 19 provide fixed indicia (fiducials) against which measurements can be made and relative to which a coordinate system can be established for the cranium and the intracranial areas. In conjunction with existing computer software developed for the system, the diagnostic images produced from the CAT scan performed with the localizing ring 17 in place will provide X, Y and Z coordinates or, in some applications, polar coordinates, for any portion of the patient's skull, brain or other tissue within the cranium which is to be investigated or treated. Such systems make it possible for example, to identify the location of a target, for example, a tumor, or the like, within the patient's brain, by X, Y and Z coordinates which define the position of the tumor, as well as its point of greatest extension within the brain tissue, etc. Since the localizing device 17 is rigidly attached to the head ring 10, which in turn is rigidly attached to the patient's head 11, the coordinates of diagnostic measurements made utilizing the localizing device 17, may be used directly as coordinates for later surgical, or other treatment, procedures performed, utilizing other appliances or instruments rigidly attached to the head ring 10 as long as the head ring remains attached in its position to the patient's head. As used in this patent, the term "diagnostic procedure" is used broadly and encompasses imaging, visualizing and localizing procedures used for diagnosis and/or treatment of cranial and/or intracranial structures. With the above procedures, the head ring 10 is applied prior to the diagnostic procedure and is continuously maintained on the patient's head during the diagnostic, surgical planning and surgical procedures. The procedures may require eight or more hours to fully complete. The continued application of the head ring to the patient during that entire time causes significant discomfort and stress to the patient.

To disconnect the imaging and treatment procedures in time which makes it possible to administer the treatments repeatedly over days and also reduces the patient's discomfort and stress, a noninvasive stereotactic adapter known as the "LAITINEN STEREOADAPTER" has been developed and is generally known and used. The "LAITINEN STEREOADAPTER" incorporates fiducial markers which can be related to CAT scans, magnetic resonance images, DSA or other images to establish an intracranial coordinate system. That coordinate system is used to relate the position of a target with respect to an isocenter or origin of the Stereotactic adapter. The "LAITINEN STEREOADAPTER" is noninvasive and is removably attached in an exactly reproducible position to the patient's head by reference to the patient's nose bridge and ear canals. Since the device also can be applied, removed and reapplied with accuracy and precision, stereotactic coordinates obtained during preoperative scanning procedures can be reproduced later during surgery with full confidence that the position of the patient's head is exactly where it was relative to the preoperative imaging studies.

The "LAITINEN STEREOADAPTER" is compatible with a "LAITINEN" head ring or arc which is used for surgical or treatment procedures and is affixed to the skull by invasive skull pins. However, the stereotactic adapter is not directly compatible with other known and widely used surgical headrings for stereotactic systems, for example, the Radionics Brown-Roberts-Wells ("BRW") stereotactic system, the Cosman, Roberts and Wells ("CRW") system, the Elekta Instruments Leksell stereotactic system and the Fischer stereotactic system. To resolve the physical incompatibility of the stereotactic adapter with other headrings, a positioning apparatus was developed which is described in the Gildenberg U.S. Pat. No. 5,423,832.

The positioning apparatus disclosed in the Gildenberg '832 patent utilizes the repositioning capability of the "LAITINEN STEREOADAPTER" to reapply and accurately position an invasive headring, for example, a "BRW"/"CRW" type headring to a patient's skull. For example, during the diagnostic procedures, the stereotactic adapter is mounted on the patient's head, and the scanning is performed. Surgical planning can then be done at a later time convenient to the persons required for planning and consultation; and a surgical procedure can be scheduled at a time and date that matches the schedules of the persons involved and the availability of the surgical facilities. At the time of surgery, the "LAITINEN STEREOADAPTER" is mounted on the patient's head in the same position that it was in during the preoperative scanning procedure. The surgical headring to be used is then mounted to the Gildenberg positioning apparatus; and the Gildenberg positioning apparatus is aligned with the "LAITINEN STEREOADAPTER", thereby positioning the surgical headring with respect to the noninvasive stereotactic adapter and the previously scanned data associated therewith. The Gildenberg positioning apparatus is designed to position its isocenter in a predetermined relationship with respect to the isocenter of the surgical headring, so that the isocenters of the surgical headring and the noninvasive stereotactic adapter coincide. To facilitate the alignment process, the positioning apparatus of the Gildenberg '832 patent is mounted with skull pins to the patient's skull to secure its aligned position while the skull pins of the surgical headring are tightened to mount and secure the surgical headring to the patient. When the pins of the surgical headring have been advanced and are firmly engaged in the patient's skull, the Gildenberg positioning apparatus and the noninvasive stereotactic adapter are removed and the patient is ready for surgery. In all stereotactic systems, the arcs or headrings used for stereotactic surgery are secured on the patient's skull using skull pins.

The positioning apparatus of the Gildenberg '832 patent provides significant advantages in, first permitting the diagnostic procedures to be conducted with noninvasive appliances and, second, permitting the diagnostic procedures to be separated in time from the surgical planning and surgery. However, the use of the Gildenberg device of the '832 patent is limited to invasive surgery, and it is not applicable to radiosurgery. If radiosurgery is being considered, the prior techniques must be used which require that the invasive headring be applied prior to the diagnostic scanning procedures and left in place during the scanning, surgical planning and surgical procedures.

As practiced today, radiosurgery uses a linear accelerator to focus a massive dose of radiation at a target or lesion in the brain. The radiation is not tissue sensitive and will damage all tissue through which it passes. Therefore, to minimize damage to healthy tissue and to target all the radiation at the lesion or tumor, as the radiation is applied, the collimator on the linear accelerator rotates through an arc having its isocenter or axis of rotation at the target, that is, the location of the lesion or tumor. The beam of radiation, therefore, sweeps through a slice of healthy tissue which exposes more tissue to the radiation, but for a shorter period of time. It is believed that even though more healthy tissue is exposed to radiation, because the time of exposure is shorter, the damage to the healthy tissue is less. Therefore, the tissue recovers more quickly and fully.

While the above radiosurgery has been shown effective, it is considered desirable to further minimize damage to healthy tissue with even less exposure to the radiation. Therefore, the radiation treatments are given over successive periods of time. Further, with each successive treatment the collimator projecting the radiation beam is rotated through a different plane with respect to the patient's head and, therefore, through different tissue with each successive arc. However, all of the axes of rotation intersect at a common point or isocenter which is the target point and location of the lesion or tumor. Therefore, the exposure of healthy tissue to the radiation is less and minimized to one treatment, whereas the target or lesion which is located at the isocenter receives the accumulation of all radiation dosages. This treatment is referred to as fractionated stereotactic radiotherapy. However, using known devices, the invasive skull pins of the surgical arc or headring must be attached to the patient and a scanning procedure and dose calculation performed with the series of treatments. While it is desirable to further stretch out the treatments over a longer period of time so that individual doses are less, the discomfort and stress of the repetitive application of the invasive skull pins of known appliances make that process impractical; and such extended and repetitive treatment procedures are not used. Therefore, there is a need to further reduce and eliminate, where possible, the discomfort and stress to a patient caused by invasive appliances, so that fractionated radiotherapy treatments extending over disconnected periods of time are practical, cost effective and acceptable.

SUMMARY OF THE INVENTION

The present invention provides a method and noninvasive apparatus for performing fractionated radiotherapy that is relatively painless to the patient. More specifically, the noninvasive alignment apparatus of the present invention replaces the invasive headrings previously used with fractionated radiotherapy and is, therefore, free of the stress and discomfort associated with the use invasive skull pins of the prior systems. The present invention has an advantage of providing more flexibility in scheduling the use of diagnostic scanning equipment and linear accelerator suites. Further, the invention allows repetitive fractionated stereotactic radiotherapy to be conducted over discontinuous periods of time and on an outpatient basis, which makes such treatments more economical, practical and acceptable to both physician and patient.

The invention further provides a method and noninvasive apparatus for performing diagnostic scanning procedure that provides scanned coordinate data that may be used with either noninvasive appliances in the performance of fractionated radiotherapy, or invasive headrings in the performance of invasive surgery.

In accordance with the principles of the present invention, a noninvasive alignment apparatus provides a stereotactic interface between a noninvasive stereotactic adapter mounted on a patient's head and a medical device. The alignment apparatus includes a frame adapted to be attached to the medical device. An adjustable rest plate is connected to the frame for noninvasively supporting at a desired elevation the patient's head with the stereotactic adapter mounted thereon. The alignment apparatus further includes first and second alignment brackets connected to opposite sides of the frame for aligning the noninvasive stereotactic adapter and the patient's head at a desired location with respect to the alignment apparatus. Noninvasive adjustable positioners are mechanically supported by the frame for maintaining the patient's head at the desired location. In another aspect of the invention, the frame has a first frame member and a second frame member. The second frame member forms a forward side of the frame and is separable from and attachable to the first frame member. Further, the frame is adapted to be selectively attached to either an imaging device or a treatment device. In a further aspect of the invention, the adjustable rest plate and first and second alignment brackets have calibrated shafts for reading and recording the desired positions of the rest plate and the brackets.

In a further embodiment of the invention, a method for performing fractionated radiotherapy comprises mounting a noninvasive stereotactic adapter on the head of a patient. The noninvasive alignment ring of the present invention is mounted to an imaging device. Next, the head of the subject with the stereotactic adapter is located within the alignment ring. Thereafter, the subject's head with the stereotactic adapter mounted thereon is adjusted to a predetermined aligned location with respect to the alignment ring. Noninvasive positioners on the alignment ring are then tightened against the patient's head to maintain it in its desired position. The diagnostic imaging procedure is then performed, and the patient's head is removed from the alignment ring and the stereotactic adapter. At a subsequent time, a radiotherapy treatment may be given by again attaching the noninvasive stereotactic adapter to the subject's head and mounting the noninvasive alignment ring to the radiotherapy machine. The subject's head with the stereotactic adapter is positioned within the alignment ring in a manner identical to that described with respect to the imaging procedure. The series of radiotherapy treatments is then given and the patient's head is removed from the alignment ring and the noninvasive stereotactic adapter. Other series of fractionated radiotherapy treatments may be given at subsequent times by repeating the above process as many times as desired.

These and other objects and advantages of the present invention will become more readily apparent during the following detailed description together with the drawings herein.

DETAILED DESCRIPTION OF THE INVENTION

Figure 1:
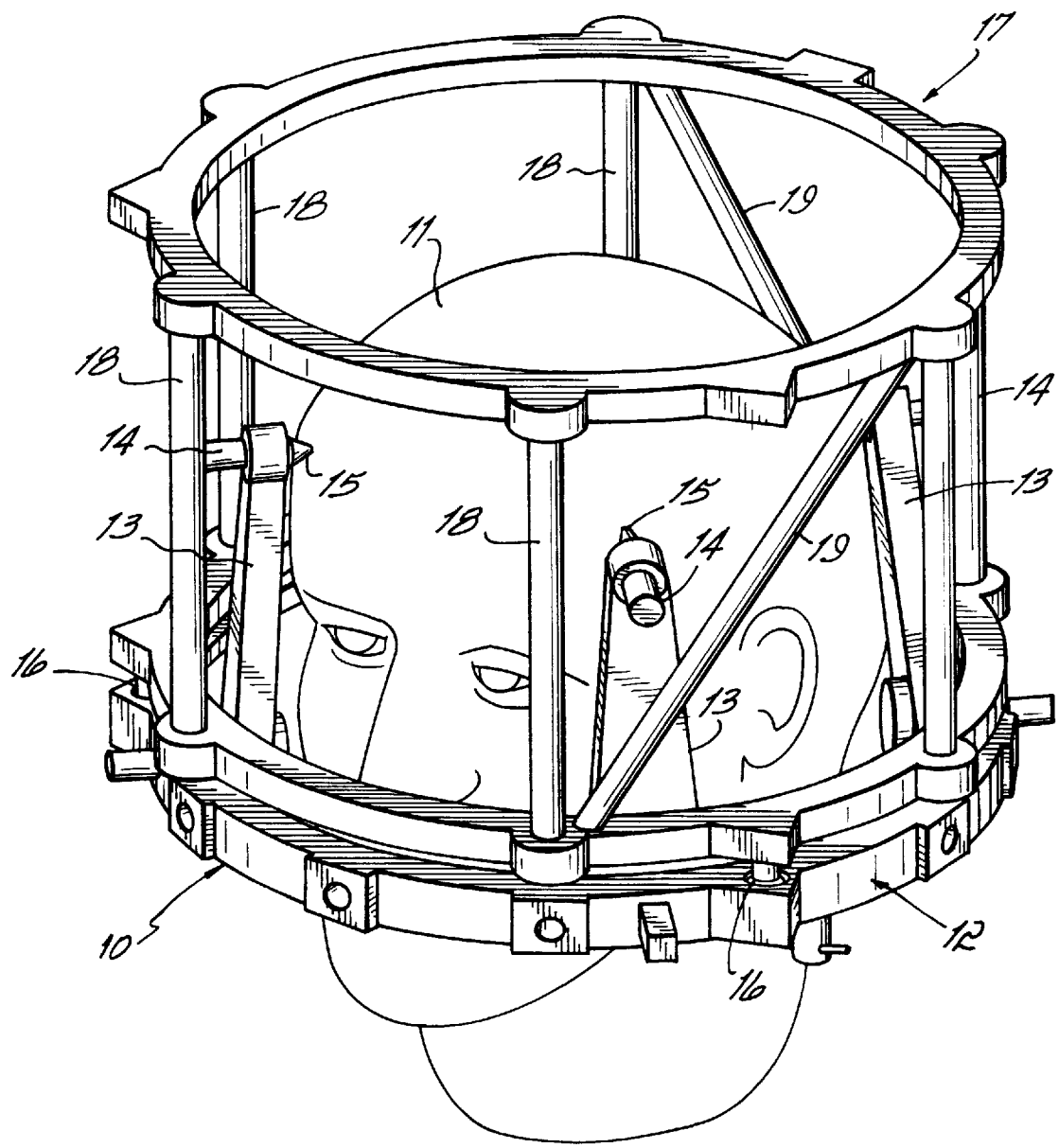
FIG. 1 is a perspective view illustrating a known "BRW"/"CRW"-type stereotactic headring attached to a patient's skull, with a known localizer ring attached to the headring.
Figure 2:
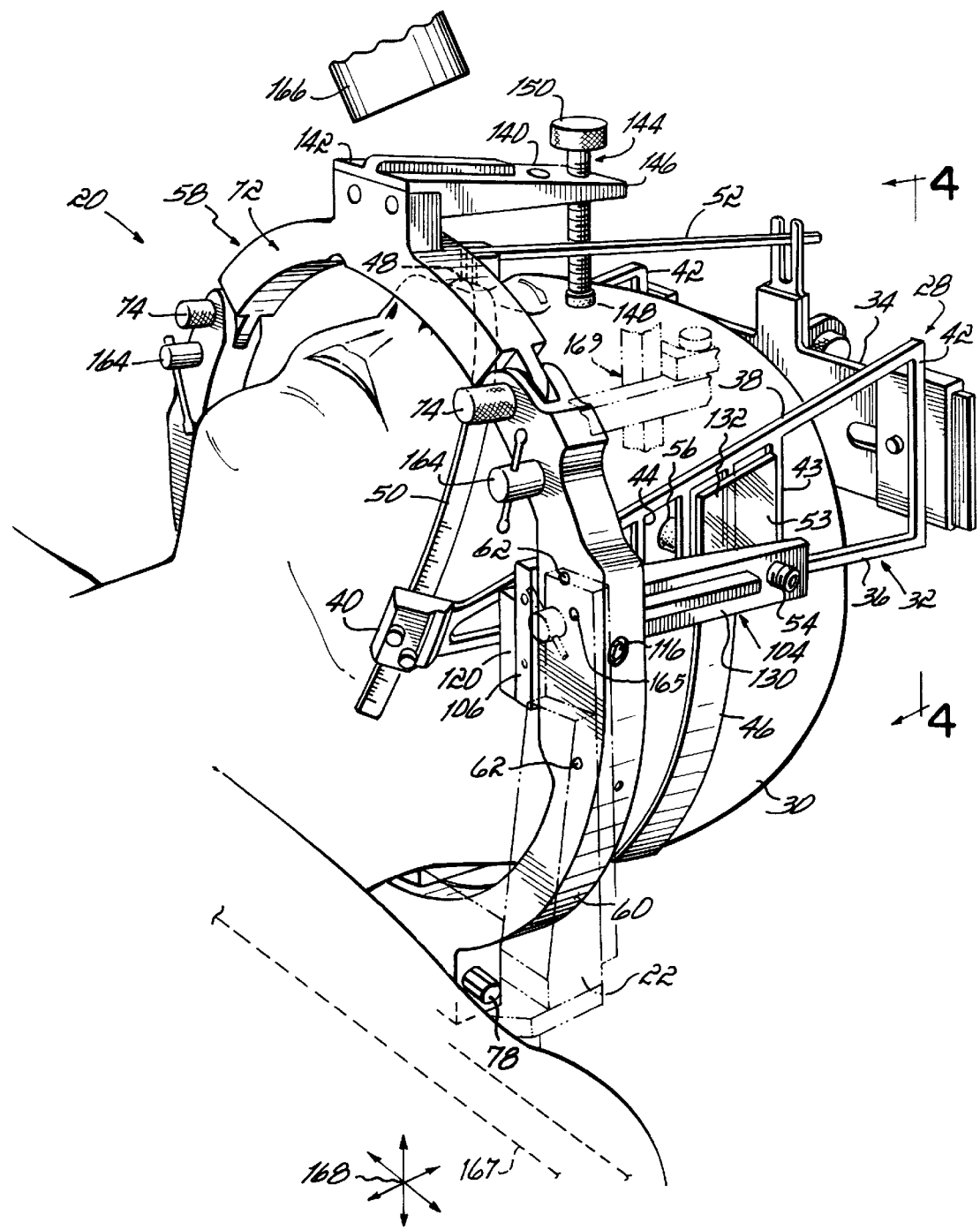
FIG. 2 is a perspective view illustrating the alignment apparatus in accordance with the principles of the present invention as it is used in radiotherapy.

Referring to FIG. 2, a noninvasive alignment device 20 is shown in operative alignment with a noninvasive stereotactic adapter 28, for example, a "LAITINEN STEREOADAPTER", which includes fiducial means or markers for establishing a coordinate or measurement system in conjunction with the diagnostic scanning and surgical procedures. The stereotactic adapter 28 has side or lateral frames 32 which are joined at one end by a plate 34. Each of the side frames 32 has a longitudinal bar 36 and an angled bar 38 that converge and are connected at one end to a coupling 40.

The bars 36, 38 are connected at their divergent opposite ends by a top bar 42 and are interconnected at predetermined points along their lengths by bridging cross members 43 which are preferably 25 millimeters ("mm") apart. The bars 36, 38, 42 and bridging cross members 43 form a fiducial or marker grid on each side of the patient's head 30.

The noninvasive stereotactic adapter 28 is positioned with respect to the patient's head by ear plugs (not shown) that are connected to cross bars 44. A rear head strap 46 is connected between the longitudinal bars 32 and a nose pad 48, shown in hidden lines. The nose pad 48 is supported by a front strap 50 and a brace 52 extending between the nose pad 48 and the plate 34. The stereotactic adapter 28 has various adjustments so that the fiducial grid bars can be positioned on the patient's head with the longitudinal bars 36 in a substantially horizontal position and the top bars 42 in a substantially vertical position. All of the supporting and attaching mechanisms for the stereotactic adapter 28 are calibrated so that when the stereotactic adapter 28 is properly positioned on the patient's head 30, the exact position of all of the adjustable members can be recorded. After the stereotactic adapter 28 is removed, it can subsequently be remounted on the patient's head in substantially the same position as before.

As will be subsequently described in more detail, the alignment apparatus 20 of the present invention is connected and fixed to a table of either a scanning machine or a linear accelerator.

The patient's head 30 with the stereotactic adapter 28 mounted thereon is positioned within the alignment apparatus 20. The alignment apparatus 20 has an adjustable head supporting rest (not shown) located behind the patient's head. The apparatus 20 also has adjustable angle plates or, alignment plates 53 for aligning the stereotactic adapter 28 with the alignment apparatus 20. The patient's head is maintained in the desired aligned position by adjusting the location of positioners 54. The positioners 54 have noninvasive pads 56 at their distal ends that contact the patient's head 30 and maintain the patient's head in its desired position within the alignment device 20. Therefore, during diagnostic procedures, the alignment apparatus 20 can be used with the stereotactic adapter and a fiducial localizing device (not shown) to first, noninvasively support, align and locate the patient's head 30 and the stereotactic adapter 28 with the imaging machine. During subsequent radiotherapy procedures, the alignment apparatus 20 may be used to support, align and locate the patient's head 30 and the stereotactic adapter 28 to a radiotherapy machine such as a linear accelerator. In addition, using the methods and apparatus previously described with respect to the Gildenberg U.S. Pat. No. 5,423,832, the data collected using the noninvasive alignment apparatus during diagnostic imaging procedures can be used for invasive surgery utilizing an invasive headring.

The noninvasive alignment apparatus 20 of the present invention is illustrated in detail in FIGS. 3–6. A support ring or frame 58 includes a first arcuate member 60 which has a plurality of tapped holes 62 for mounting the member 60 to mounting plate 59 of a medical device, for example, an imaging machine. The member 60 includes three patterns of the holes 62 which are separated by approximately ninety degrees so that the ring may be mounted as illustrated in FIG. 2 or, alternatively, rotated approximately ninety degrees either clockwise, or counterclockwise, with respect to the centerline 61 of the headring 58 as is desired. The frame centerline 61 extends in a direction perpendicular to a plane passing through an annular surface 63 of the support ring 58. The ends 64, 65 of the first arcuate member 60 contain grooves 66 which are sized and shaped to received tongues 68 on the ends 70 of a second arcuate member 72 forming a forward side of the support ring 58. Hinge screws 74 extend through respective clearance holes in one side of the slots 66 and the tongues 68 and are threaded into respective opposite sides of the slots 66. The heads of the screws 74 are knurled to facilitate the screws 74 being manually unscrewed, removed and subsequently refastened to the first arcuate member 60. When one of the screws 74 is removed from one end 65 of the first arcuate member 60, the second arcuate member 72 functions as a hinged section of the support ring 58. The hinged section 72 is free to pivot with respect to the other screw 74 functioning as a hinge at the end 66 of the first arcuate member 60 as shown in phantom in FIG. 3. If, instead, the screw 74 at the end 64 is removed, the hinged section 72 will pivot with respect to the end 65. Opening the support ring 58 facilitates the insertion of the patient's head 30 with the attached stereotactic adapter 28 within the alignment apparatus 20.

Figure 3:
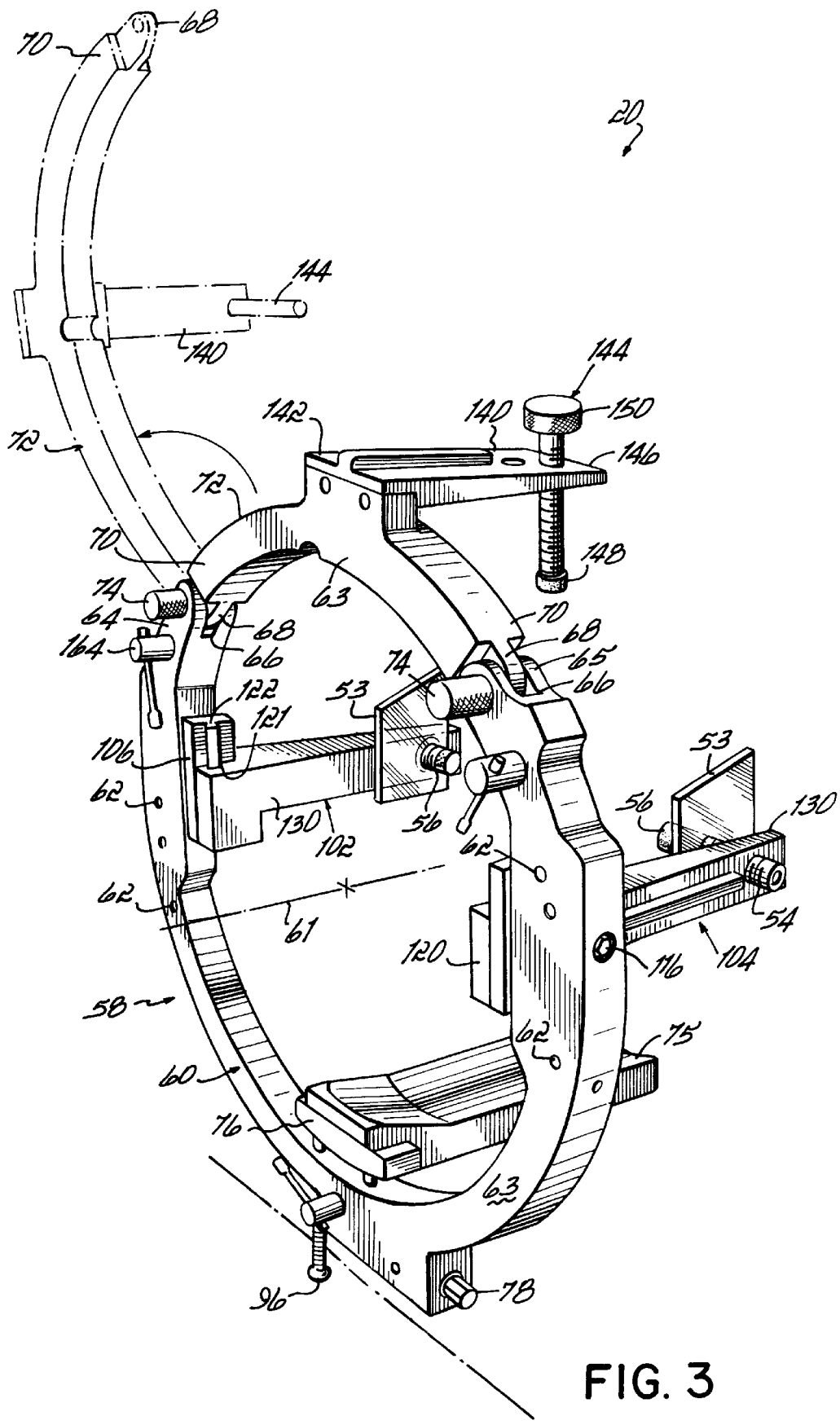
FIG. 3 is a perspective view of the alignment apparatus.
Figure 4:
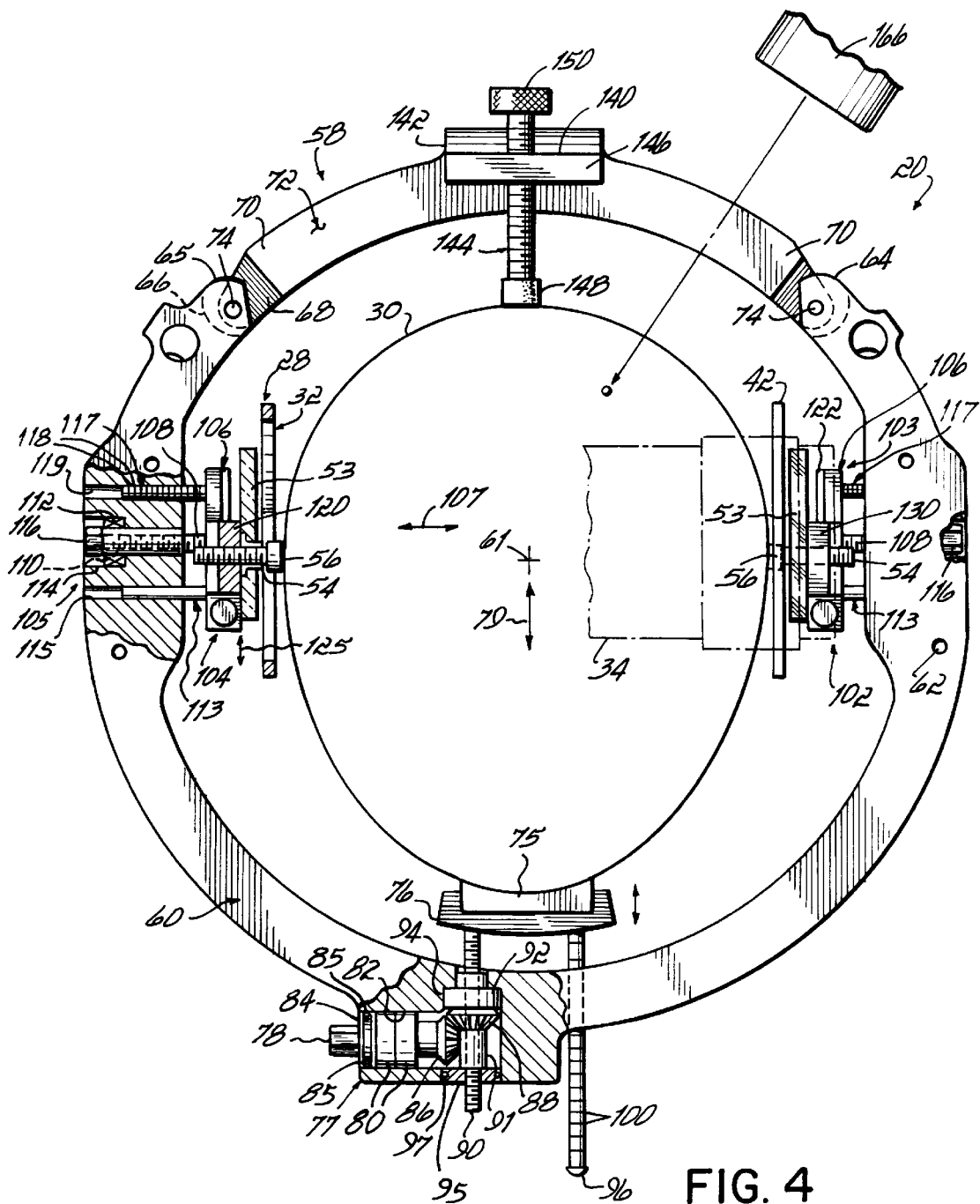
FIG. 4 is a rear view of the alignment apparatus taken along view line 4—4 of FIG. 2.

Referring to FIGS. 3 and 4, the patient's head 30 is preferably generally centered within the support ring 58. The head is supported at the preferred elevation by means of an occipital rest or plate 75 which is connected to an adjustable posterior rest 76. A posterior position adjusting mechanism 77 connects the posterior rest to a rear side of the support ring 58 and, permits the occipital rest to be selectively moved in a direction 79 toward and away from, and preferably, radially with respect to the frame centerline 61. The posterior position adjusting mechanism 77 is operated by turning an occipital rest drive shaft 78. The shaft 78 preferably has a hexagonal head at one end that is sized to mate with a socket wrench. The drive shaft 78 is mounted within inner races of two ball bearings 80 which have their outer races press fit into a bore 82 of the arcuate member 60. A cap 84 extends over one end of the drive shaft 78 and is secured in place at the open end of the bore 82 by screws 85. A bevel or miter gear 86 is connected to the other end of the drive shaft 78 and mates with a second bevel or miter gear 88. The miter gear 88 is rigidly connected to a cylindrical nut 91 that, in turn, is threaded over an occipital rest adjuster screw 90. The miter gear 88 is mounted within an inner race of a bronze sleeve bearing 92 that has its an outer race press fit into a bore 94 of the first arcuate member 60. One end of the screw 90 extends through a cap 95 which is held in place by screws 97. The occipital rest adjuster screw 90 has one end rigidly connected to the posterior rest 76. Therefore, rotation of the drive shaft 78 rotates the miter gears 86, 88 and cylindrical nut 91. The miter gear 88 and nut 91 are restrained from linear motion; and therefore, rotation of nut 91 over screw 90 will cause longitudinal motion of the adjuster screw 90 and moves the occipital rest plate 75 in a generally radial direction with respect to the frame centerline 61. A graduated indicator shaft 96 extends through a bore 98 within the arcuate member 60 and has one end connected to the posterior rest 76. The graduated indicator shaft 96 also moves in a generally radial direction and follows the motion of the posterior rest 76. Therefore, when the occipital rest 75 is supporting the patient's head 30 in the desired position, a count of the exposed gradations 100 on the shaft 96 can be recorded. The recorded count is used to adjust the position of the occipital rest 75 during a subsequent procedure in order to locate the patient's head 30 at the same position.

To further facilitate properly positioning the patient's head 30 and stereotactic adapter 28 within the support ring 58, the alignment apparatus 20 includes alignment brackets 102, 104 which are located on diametrically opposite sides of the support ring 58. Position adjusting mechanisms 103, 105 mechanically couple the alignment brackets 102, 104, respectively, to the support frame 58, and operation of the position adjusting mechanisms 103, 105 move the respective alignment brackets 102, 104 in a direction 107 toward and away from the frame centerline 61, that is, in a generally radial direction with respect to the support ring 58. Each of the position adjusting mechanisms 103, 105 is identical and therefore, only mechanism 105 is described in detail. One end of a lateral drive screw 108 is rigidly connected to a lateral block 106 located at a base end of the alignment bracket 102. The lateral drive screw 108 is threaded into a drive bushing 110 which is rotatably mounted within a bushing or bearing 112 located within a bore 114 of the ring 58. The threaded sleeve 110 has a hexagonal head 116 connected at one end which is recessed into the side of the support ring 58. The sleeve 110 is rotatably mounted in the bushing 112 but is prevented from moving in a longitudinal direction. Therefore, when the hexagonal nut 116 is rotated using a socket wrench, the sleeve 110 rotates which is effective to moves the drive screw 108 and lateral block 106 in a generally radial direction with respect to the support ring 58. A calibrated shaft 117 having graduations 118 is disposed in a bore 119 and has one end rigidly connected to the lateral block 106. Therefore, the position of the alignment bracket 104 as represented by the number of exposed graduations can be read and recorded. A guide rod 113 is mounted within the bore 115 to facilitate the motion of the lateral block 106 and alignment bracket 104.

Figure 5:
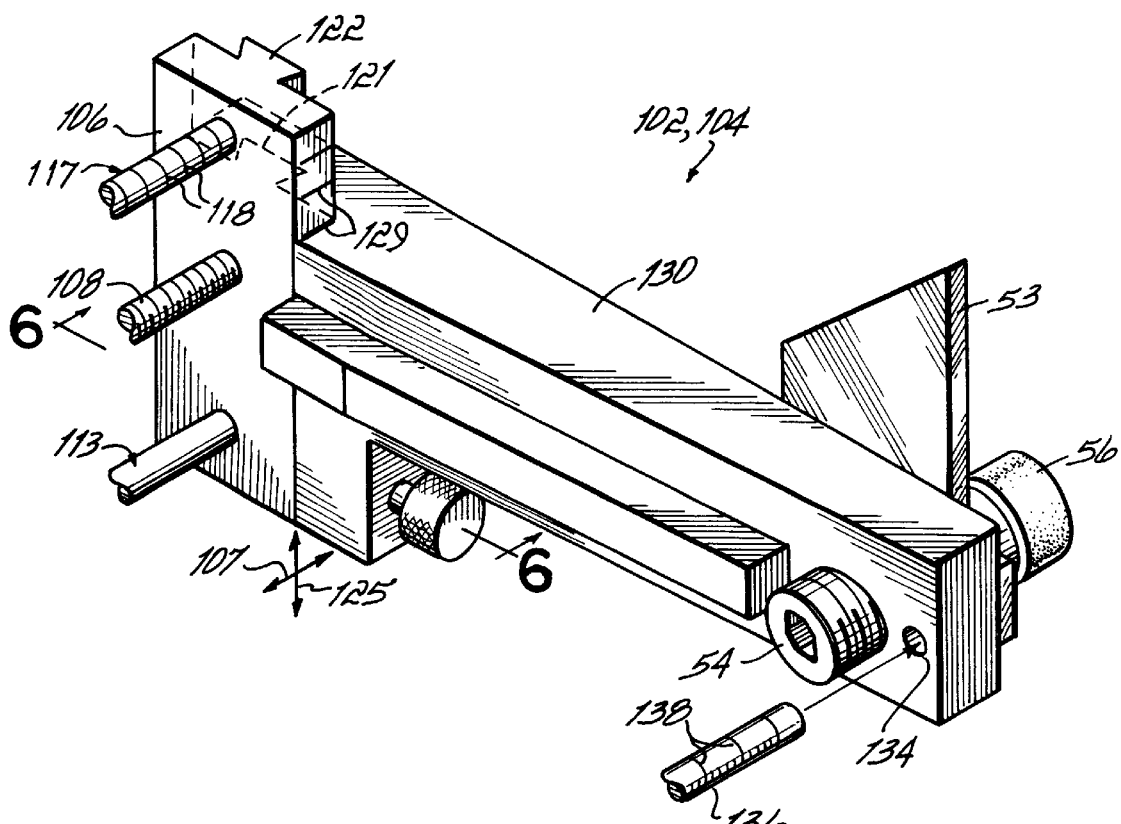
FIG. 5 is a perspective view of a one of the side brackets of the positioning apparatus of the present invention.
Figure 6:
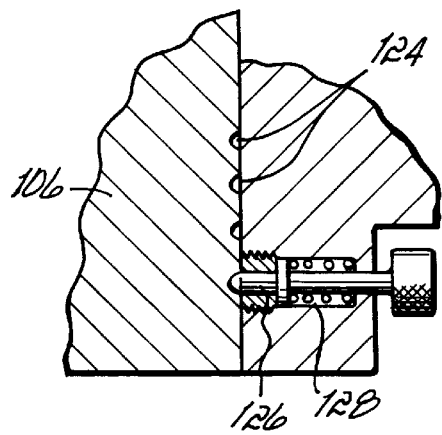
FIG. 6 is a partial cross-sectional view taken along line 6—6 of FIG. 5.

Referring to FIG. 5, each of the alignment brackets 102, 104 is mounted to slide on a respective lateral block 106. Each of the brackets 102, 104 has a base 120 with a dovetail shaped slot 121 that mates with the dovetail shaped projection 122 of its respective lateral block 106. Therefore, the each of the alignment brackets 102, 104 is guided in its motion on the respective lateral block 106 in a direction 125 that is first, generally perpendicular to the other direction of motion 107 of the alignment brackets 102, 104 and second, generally parallel to the direction of motion 79 (FIG. 4) of the occipital rest 75. As shown in FIG. 6, the lateral block 106 has a number of holes 124 which are sized and shaped to receive the end of a pin 126. The pin 126 is biased toward the holes 124 by a compression spring 128. Preferably, the holes 124 are spaced approximately 5 mm apart, and the lateral displacement of the alignment brackets 102, 104 is measured by the graduations 129 (FIG. 5) on the lateral block 106. Each of the lateral brackets 102, 104 has a lateral bar 130 that is connected at one end to the base 120 and is generally parallel to the frame centerline 61. The alignment plates 53 are connected to the distal ends of the lateral bars 130 of the respective alignment brackets 102, 104 by screws or other fasteners. The positioners 54 are adjusting screws that have pads 56 mounted on one end, and the adjusting screws 54 are threaded through the bars 130 and move parallel to the direction of motion 107, that is, toward and away from the frame centerline 61. To measure the final position of the positioners 54, each of the bars 130 has a hole 134 (FIG. 5) adjacent the positioners 54 A calibrated shaft 136 has graduations 138 for measuring the extension of the positioners 54 through the respective lateral bars 130. Preferably, the calibrated shaft 136 is located on one end of a wrench that is used to operate the position adjusting mechanisms 77, 103, 105 and positioners 54.

Referring to FIGS. 3 and 4, the support ring 58 further has an anterior block 140 connected to an anterior rest plate 142 which in turn is rigidly connected to the hinged section 72. Preferably, the anterior block 140 is located diametrically opposite the occipital rest 75. An anterior adjusting screw 144 is threaded through the distal end 146 of the anterior block 140. The anterior adjusting screw 144 has a pad 148 mounted on an inner end thereof and has a knurled knob 150 on its opposite end.

Figure 7:
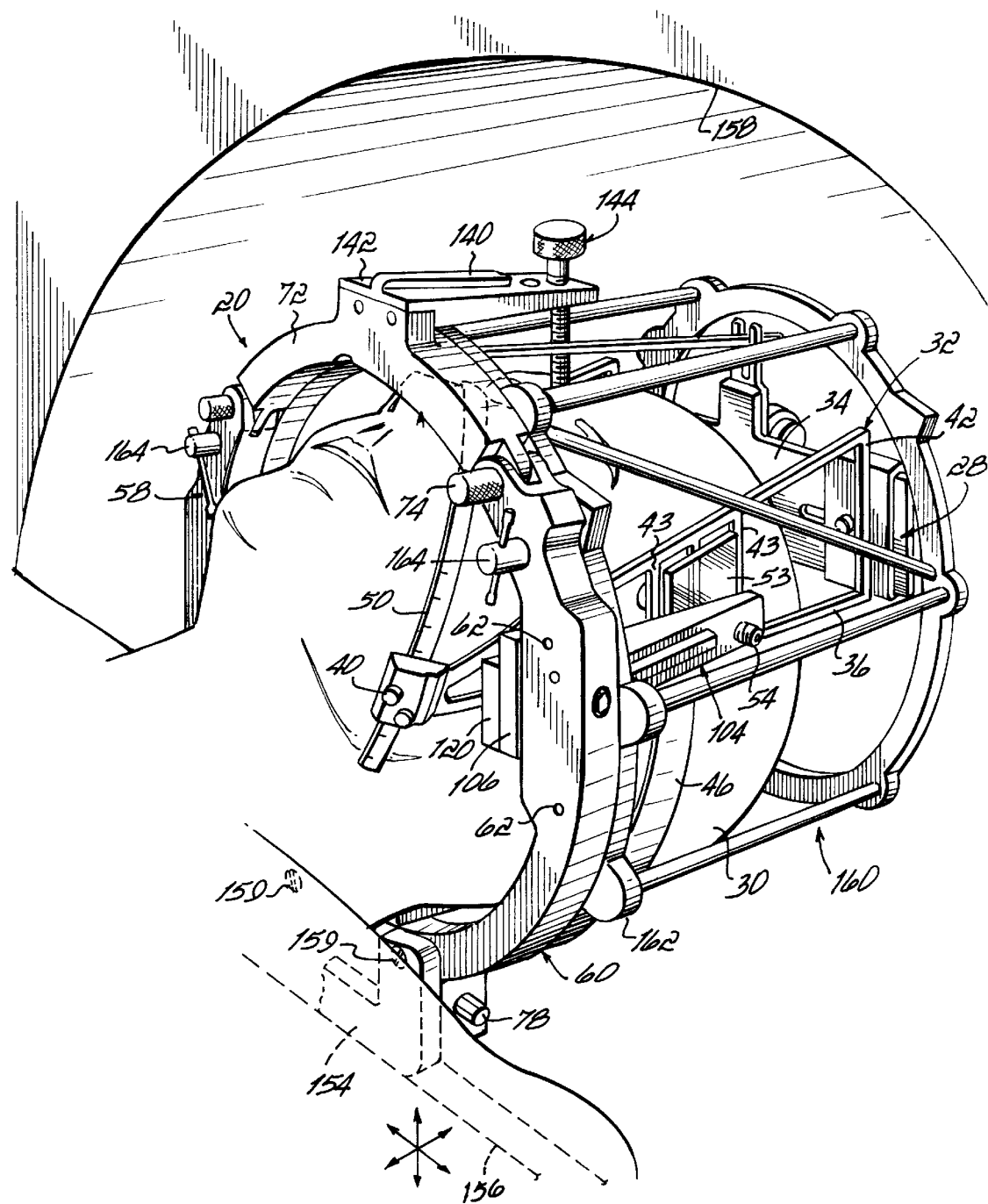
FIG. 7 is a perspective view illustrating the alignment apparatus in accordance with the principles of the present invention as it is used in diagnostic procedures.

Referring to FIG. 7, the alignment apparatus 20 is illustrated as used in a preoperative diagnostic procedure. First, the noninvasive stereotactic adapter 28 is mounted on the patient's head 30 in accordance with its normal usage. After the stereotactic adapter 28 is in place, the positions of its various adjustments are recorded in a known manner for later use. Next, alignment apparatus 20 is attached to a mounting plate 154 at the head end of a table 156 associated with a scanning machine 158, for example, by screwing fasteners 159 into the lowermost pattern of holes 62 of the support ring 58. The scanning machine is of the type that produces CAT scan images. After the support ring 58 has been attached to the plate 154, one of the hinge screws 74 is removed and the hinged section 72 is pivoted about the other of the hinge screws 74 to open the top side of the support ring 58. Opening the support ring 58 facilitates the positioning of the patient's head 30 with the stereotactic adapter 28 mounted thereon inside the alignment apparatus 20.

The patient's head 30 is manually lowered to a position within the support ring 58. The patient's head 30 is then manually supported at the desired central location within the support ring 58. The drive shaft 78 is rotated to raise or lower the occipital rest 75 and place the patient's head 30 at a desired generally central elevation within the support ring 58. Thereafter, the nuts 116 are turned to move the left and right alignment brackets 102, 104 in a generally radial direction to position the patient's head 30 centrally therebetween. The alignment brackets 102, 104 are moved toward and positioned in close proximity to the fiducial bars 36, 38 of the stereotactic adapter 28. Thereafter, the different adjusting screws and nuts 78, 116 are turned and the patient's head is manipulated so that the non-parallel edges of the alignment plates 53 align precisely with but do not contact the outer edges of the fiducial bars 36, 38 of the stereotactic adapter 28. Preferably, so that the alignment of the stereotactic adapter 28 on the patient's head 30 is not disturbed, the alignment plates 53 should align closely with but not touch the bars or other components of the stereotactic adapter 28. When the edges of the plates 53 and the bars 36, 38 are precisely aligned with each other, the lateral positioning screws 54 and are tightened to locate their respective pads 56 against the outside of the patient's head 30. The positioners 54 locate the alignment apparatus 20 with respect to the stereotactic adapter 28 and in turn the patient's head 30. When it is properly mounted, the isocenter, that is, the origin or measurement reference point, of the aligning apparatus 20 is coincident with the isocenter of the stereotactic adapter 28.

Thereafter, a localizing device or fiducial localizer 160 is attached to the aligning apparatus 20. In a known manner, ball connectors (not shown) extending from the bottom side of the lower ring 162 of the localizing device 160 are inserted into bores (not shown) on an adjacent side of the support ring 58. Cam locks 164 are used to lock the ball connectors of the localizing device 160 into the bores of the support ring 58. The localizing device 160 provides fiducials in the scanned data that are required to do surgical planning for subsequent radiotherapy. The alignment apparatus 20 provides an accurate and repeatable alignment between the fiducial localizer 160 and the noninvasive stereotactic adapter 28, thereby permitting the scanning to be done with a minimum of discomfort to the patient.

After the localizing device 160 is attached to the alignment apparatus 20, the hinged section 72 is pivoted back into alignment with the support ring 58, and the screw 74 that was removed is reattached to connect the separated ends of the hinged section 72 and the support ring 58. The screw 144 in the anterior block 140 is tightened to located the pad 148 at the end of the screw 144 on the patient's forehead. At this point, the stereotactic adapter 28, alignment apparatus 20 and localizing device 160 are all aligned with the scanning machine 158. The positions of the various elements of the alignment apparatus 20 as represented by the calibrated shafts 96, 117, 136 and graduation lines 129 are read and recorded for subsequent use. The scanning machine 158 is then operated to produce the desired scanned data that will include the desired fiducials. For example, data will be obtained that represents scans through the isocenter of the stereotactic adapter 28 and scans through the desired target (s), that is, scans through the lesion or tumor of interest. The above procedure has the advantage of using noninvasive appliances to produce scanned data that may be used either for invasive surgery or for fractionated radiotherapy.

FIG. 2 illustrates the use of the alignment apparatus 20 in association with a linear accelerator for performing fractionated radiotherapy. The noninvasive stereotactic adapter 28 is mounted on the patient's head in the known manner using the positions that were recorded when the stereotactic adapter 28 was mounted on the patient's head during the scanning process. The alignment apparatus 20 is connected to a goal post bracket 22 at the head end of patient support couch 167 by using, for example, screws extending into threaded holes 165 in the alignment apparatus 20. In a manner identical to that previously described with respect to FIG. 7, the patient's head 30 with the stereotactic adapter attached is inserted within and aligned with the alignment apparatus 20. The couch 167 is then rolled to a docking location which locks the couch in the desired alignment with the isocenter of the collimator 166 of the linear accelerator, for example, an "X-KNIFE" commercially available from Radionics of Burlington, Mass. Next, using the cam locks 164, a fiducial system 169 associated with the "X-KNIFE" shown in phantom and indicating the target isocenter is attached to the head ring 58. The headring 58 permits the fiducial system 169 to be accurately and repetitively aligned to the stereotactic adapter 28 so that the radiotherapy can be conducted over successive periods of time without the use of invasive skull pins. The couch 167, which is movable in three mutually perpendicular axes of motion 168, is then adjusted to bring the target isocenter into coincidence with the isocenter of the linear accelerator, that is, the target point of the radiation. The couch 167 is rotated to a first angular position with respect to a vertical axis of rotation passing through the isocenter of the collimator; and a radiation treatment is given. A calibrated scale is associated with that rotation of the couch so that the couch can be moved to, and locked, with respect to the desired angular position. Preferably, a series of radiation treatments is given with the couch in different angular positions, so that the collimator projects the beam of radiation through different slices of tissue. The patient is then removed from the alignment apparatus 20; the stereotactic adapter 28 is removed; and the patient can return home. At a subsequent time, the above process is repeated; and another series of radiation treatments is given. Most often, the radiotherapy treatments are given at the same angles, however, sometimes different angles are used with repetitive treatments; and if desired, the target isocenter may be adjusted. The above process may be repeated any number of subsequent times without stress or discomfort to the patient from the application of the headring. By minimizing the stress and discomfort associated with the application of the headring, the invention has the advantage of permitting fractionated radiotherapy treatments to be given over different periods. For the first time, repetitive fractionated radiotherapy treatments given over different periods of time can be performed on an outpatient basis and therefore, are practical and acceptable to both the patient and the physician. By allowing repetitive treatments, the invention has a further advantage of providing more flexibility in that the angle of the dosage and the target isocenter may be changed during the repetitive treatments.

While the invention has been set forth by a description of the preferred embodiment in considerable detail, it is not intended to restrict or in any way limit the claims to such detail. Additional advantages and modifications will readily appear to those who are skilled in the art. For example, the lengths of the alignment brackets 102, 104 may be varied to accommodate heads of different sizes. Further, while preferably, the support ring 58 is circular, it can have other shapes, for example, oval, octagonal, or other multilateral shapes. In addition, while the position adjusting mechanisms 103, 105 are located diametrically opposite each other on the support ring 58, those mechanisms may have other locations and take other forms so long as they perform the function of permitting the alignment plates 53 to be aligned with the stereotactic adapter 28. The headring 58 is described and illustrated as used with a CAT scanning machine, however, minor changes to the headring 58 may be made to make it compatible with an MRI scanner or other scanning machines. In addition, the headring 58 may be modified so that it can be used with other noninvasive stereotactic adapters and fiducial systems than those illustrated and described herein.

The invention, therefore, in its broadest aspects, is not limited to the specific detail shown and described. Consequently, departures may be made from the details described herein without departing from and scope of the claims which follow:

What is claimed is:

1. A noninvasive stereotactic apparatus for aligning a noninvasive stereotactic adapter mounted on a patient's head with a medical device, the apparatus comprising:
   a frame adapted to be mounted with respect to the medical device, the frame having a frame centerline;
   a rest plate connected to the frame for noninvasively supporting the patient's head at a desired elevation;
   a first alignment bracket having a length generally parallel to the frame centerline and being movably mounted to the frame, the first alignment bracket being movable in a first direction toward and away from the frame centerline for aligning the noninvasive stereotactic adapter and the patient's head at a desired location with respect to the medical device; and
   noninvasive movable positioners mechanically supported by the frame for maintaining the patient's head at the desired location.

2. The noninvasive stereotactic apparatus of claim 1 wherein the frame comprises:
   a first frame member; and
   a second frame member forming a forward side of the frame between the opposite sides and being separable from and attachable to the first frame member.

3. The noninvasive stereotactic apparatus of claim 2 wherein the second frame member has one end pivotally connected to one end of the first frame member.

4. The noninvasive stereotactic apparatus of claim 3 wherein the first and second frame members form a generally circular frame.

5. The noninvasive stereotactic apparatus of claim 2 wherein the frame further includes a forward positioner connected to the second frame member at a location generally opposite the rest plate, the forward positioner further functioning to maintain the patient's head at the desired location.

6. The noninvasive stereotactic apparatus of claim 1 further comprising a first position adjusting mechanism connecting the first alignment bracket to the frame for selectively moving the first alignment bracket in the first direction.

7. The noninvasive stereotactic apparatus of claim 5 further comprising a second alignment bracket movably mounted to the frame at a location generally opposite the first alignment bracket, the second alignment bracket having a length generally parallel to the frame centerline and being movable in a second direction toward and away from the frame centerline.

8. The noninvasive stereotactic apparatus of claim 1 further comprising a second position adjusting mechanism connecting the second alignment bracket to the frame for selectively moving the second alignment bracket in the second direction.

9. The noninvasive stereotactic apparatus of claim 8 wherein the first and second directions are parallel.

10. The noninvasive stereotactic apparatus of claim 9 wherein the first and second directions are colinear.

11. The noninvasive stereotactic apparatus of claim 8 wherein each of the alignment brackets comprises:
    a lateral bar having a base end and a distal end and longitudinally oriented in a direction generally parallel to the frame centerline; and
    an alignment plate connected to a distal end of the lateral bar.

12. The noninvasive stereotactic apparatus of claim 11 wherein each of the first and second position adjusting mechanisms includes a screw drive operatively coupled between the frame and the base end of a lateral bar for moving a respective alignment bracket toward and away from the frame centerline.

13. The noninvasive stereotactic apparatus of claim 12 wherein each of the first and second position adjusting mechanisms further comprises a lateral block connected to the screw drive and mechanically coupled to the base end of a respective lateral bar to guide motion of the alignment bracket in a direction generally perpendicular to both the first direction and the frame centerline.

14. The noninvasive stereotactic apparatus of claim 13 further comprising a lock connected between the base end of each of the lateral bars and a respective lateral block for locking the lateral bar and the respective alignment bracket with respect to the respective lateral block.

15. The noninvasive stereotactic apparatus of claim 11 wherein each of the noninvasive positioners is connected to a lateral bar.

16. The noninvasive stereotactic apparatus of claim 15 wherein each of the noninvasive positioners comprises:
    a screw threadedly engaged with the distal end of a respective lateral bar; and
    a noninvasive pad connected to an end of the screw directed toward the frame centerline, the noninvasive pad being configured for contacting and maintaining the patient's head in a desired position.

17. The noninvasive stereotactic apparatus of claim 15 further comprising a calibrated shaft positionable with respect to each of the positioners for measuring an extension of a respective positioner toward the frame centerline.

18. The noninvasive stereotactic apparatus of claim 1 further comprising a position adjusting mechanism connecting the rest plate to the frame for selectively moving the rest plate toward and away from the frame centerline.

19. The noninvasive stereotactic apparatus of claim 18 wherein position adjusting mechanism further includes a calibrated shaft for measuring a position of the position adjusting mechanism with respect to the frame.

20. The noninvasive stereotactic apparatus of claim 1 wherein the frame further includes connectors for receiving and securing compatible connectors of a fiducial localizer.

21. A noninvasive stereotactic apparatus for aligning a noninvasive stereotactic adapter mounted on a patient's head with a medical device, the apparatus comprising:

a frame having opposite sides and adapted to be mounted with respect to the medical device, the frame including
a first frame member, and
a second frame member forming a forward side of the frame between the opposite sides, the second frame member being separable from and having one end pivotally connected to the first frame member;

first and second alignment brackets connected to the opposite sides of the frame for aligning the noninvasive stereotactic adapter and the patient's head at a desired location with respect to the medical device; and noninvasive movable positioners mechanically supported by the frame for maintaining the patient's head at the desired location.

22. A method of performing stereotactic fractionated radiotherapy comprising:

a) mounting a noninvasive stereotactic adapter on a head of a subject;

b) locating the head of the subject within a noninvasive alignment ring operatively positioned with respect to a collimator of a radiotherapy machine;

c) moving the stereotactic adapter and the subject's head to a predetermined location with respect to the alignment ring;

d) coupling a fiducial device associated with the radiotherapy machine to the alignment ring;

e) performing a radiotherapy treatment using the radiotherapy machine;

f) removing the patient's head from the noninvasive alignment ring and the noninvasive stereotactic adapter, whereby the radiotherapy treatment is performed using noninvasive appliances.

23. The method of claim 22 wherein after the step of locating the head of the patient within the alignment ring, the method further comprises the step of noninvasively holding the subject's head at the predetermined location using the alignment ring.

24. The method of claim 23 further comprising the step of iterating steps a) through f) at a subsequent time to perform another radiotherapy treatment using the radiotherapy machine using noninvasive appliances of radiation therapy treatments.

25. A noninvasive stereotactic apparatus for aligning a noninvasive stereotactic adapter mounted on a patient's head with a medical device, the apparatus comprising:

a frame adapted to be mounted with respect to the medical device, the frame having a frame centerline;

a rest plate connected to the frame for noninvasively supporting the patient's head at a desired elevation;

a first alignment bracket having a length generally parallel to the frame centerline and being movably mounted to the frame, the first alignment bracket being movable in a direction generally perpendicular to the frame centerline and generally parallel to a plane defined by the frame for aligning the noninvasive stereotactic adapter and the patient's head at a desired location with respect to the medical device; and noninvasive movable positioners mechanically supported by the frame for maintaining the patient's head at the desired location.

* * * * *

UNITED STATES PATENT AND TRADEMARK OFFICE
CERTIFICATE OF CORRECTION

PATENT NO. : 5,855,582
DATED : January 5, 1999
INVENTOR(S) : Gildenberg

It is certified that error appears in the above-indentified patent and that said Letters Patent is hereby corrected as shown below:

In the Specification

In column 7, line 27, before "outer", delete "an".
In column 8, line 6, delete "moves", and insert therefor --move--.
In column 8, line 19, after "Therefore,", delete "the".
In column 9, line 32, after "54", delete "and".
In column 9, line 59, delete "located", and insert therefor --locate--.
In column 11, line 24, after "departing from", insert --the spirit--,

In the Claims

In claim 7, column 12, line 1, delete "5", and insert therefor --6--;

In claim 8, column 12, line 8, delete "1", and insert therefor --7--;

Signed and Sealed this

Third Day of August, 1999

Attest:

Q. TODD DICKINSON

*Attesting Officer*   *Acting Commissioner of Patents and Trademarks*